United States Patent [19]

Kawaguchi et al.

[11] 4,108,725

[45] Aug. 22, 1978

[54] ANTIBIOTIC COMPLEX

[75] Inventors: Hiroshi Kawaguchi, Tokyo; Koji Tomita, Kawasaki; Kei-ichi Fujisawa, Kamifukuoka; Hiroshi Tsukiura, Mitaka, all of Japan

[73] Assignee: Bristol-Myers Company, New York, N.Y.

[21] Appl. No.: 714,202

[22] Filed: Aug. 13, 1976

Related U.S. Application Data

[60] Division of Ser. No. 627,391, Oct. 30, 1975, Pat. No. 4,012,576, which is a continuation-in-part of Ser. No. 532,137, Dec. 12, 1974, abandoned.

[51] Int. Cl.$^2$ .............................................. C12D 9/20
[52] U.S. Cl. ...................................................... 195/96
[58] Field of Search .......................................... 195/96

[56] References Cited

U.S. PATENT DOCUMENTS 3,136,704   6/1964   Charney .............................. 195/80 R

*Primary Examiner*—Lionel M. Shapiro
*Attorney, Agent, or Firm*—David M. Morse

[57] ABSTRACT

A novel aminoglycoside antibiotic complex designated herein as Bu-2183 is produced by fermentation of *Pseudomonas* sp. strain D946-B83, A.T.C.C. 31086. Complex Bu-2183 is known to consist of at least five components, said components being herein designated Bu-2183 A, $A_2$, B, C and D. The complex and the individual aminoglycoside components Bu-2183 A, $A_2$, and B are found to have a broad spectrum of antibacterial activity and are especially useful in inhibiting aminoglycoside-resistant organisms including *Pseudomonas* species.

3 Claims, 8 Drawing Figures

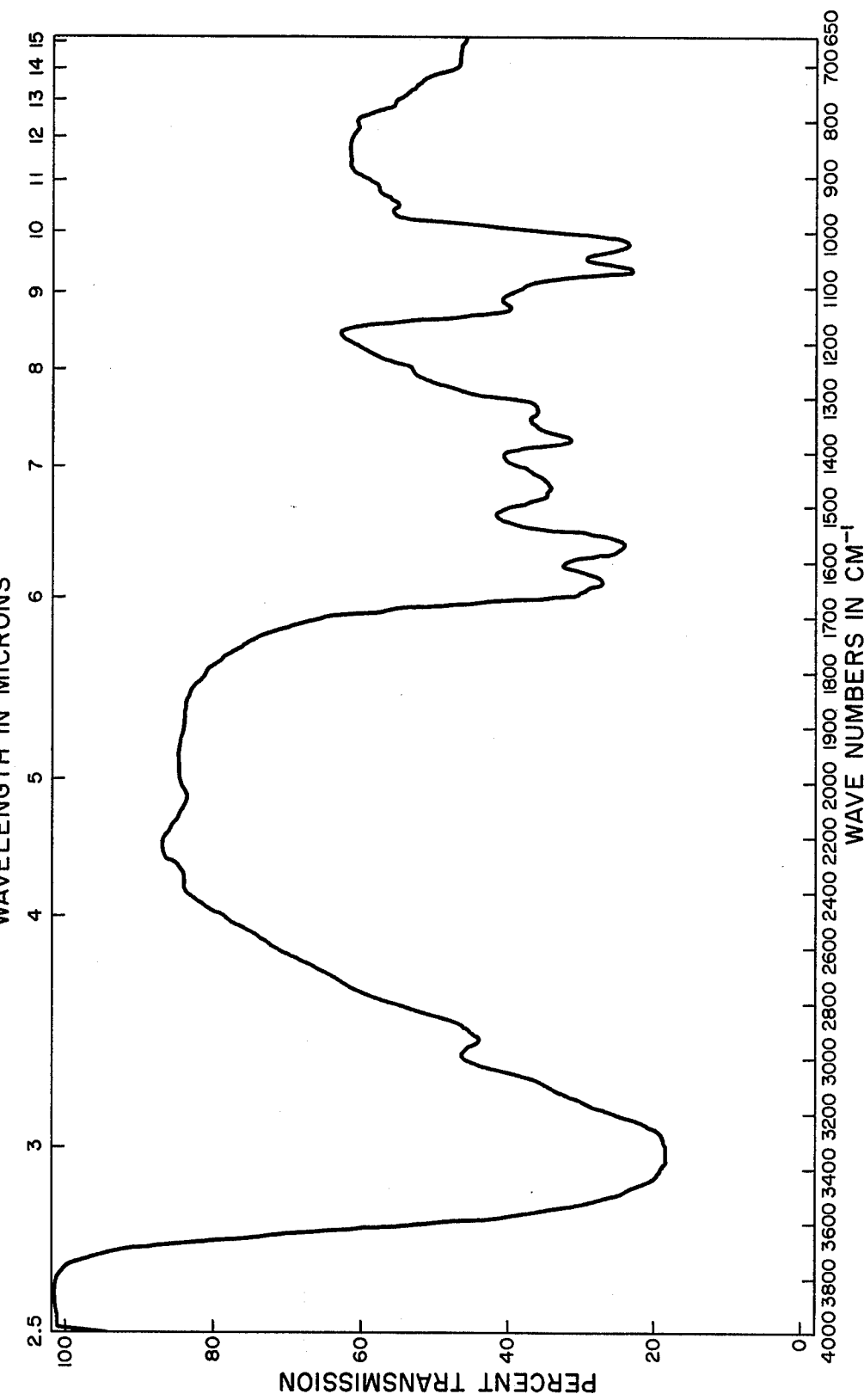

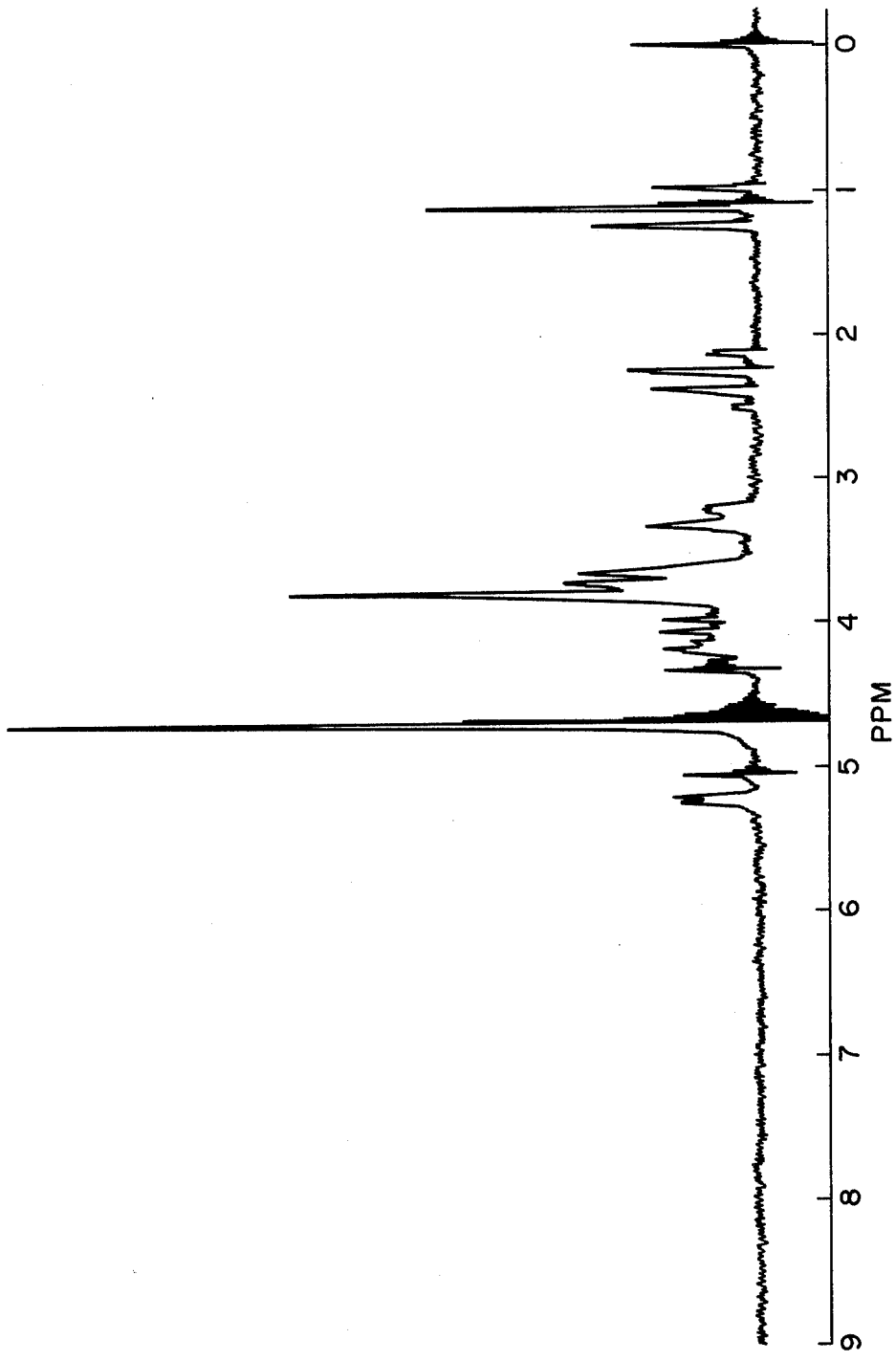
FIG. 2 NUCLEAR MAGNETIC RESONANCE SPECTRUM OF BU-2183A HYDROCHLORIDE IN D₂O

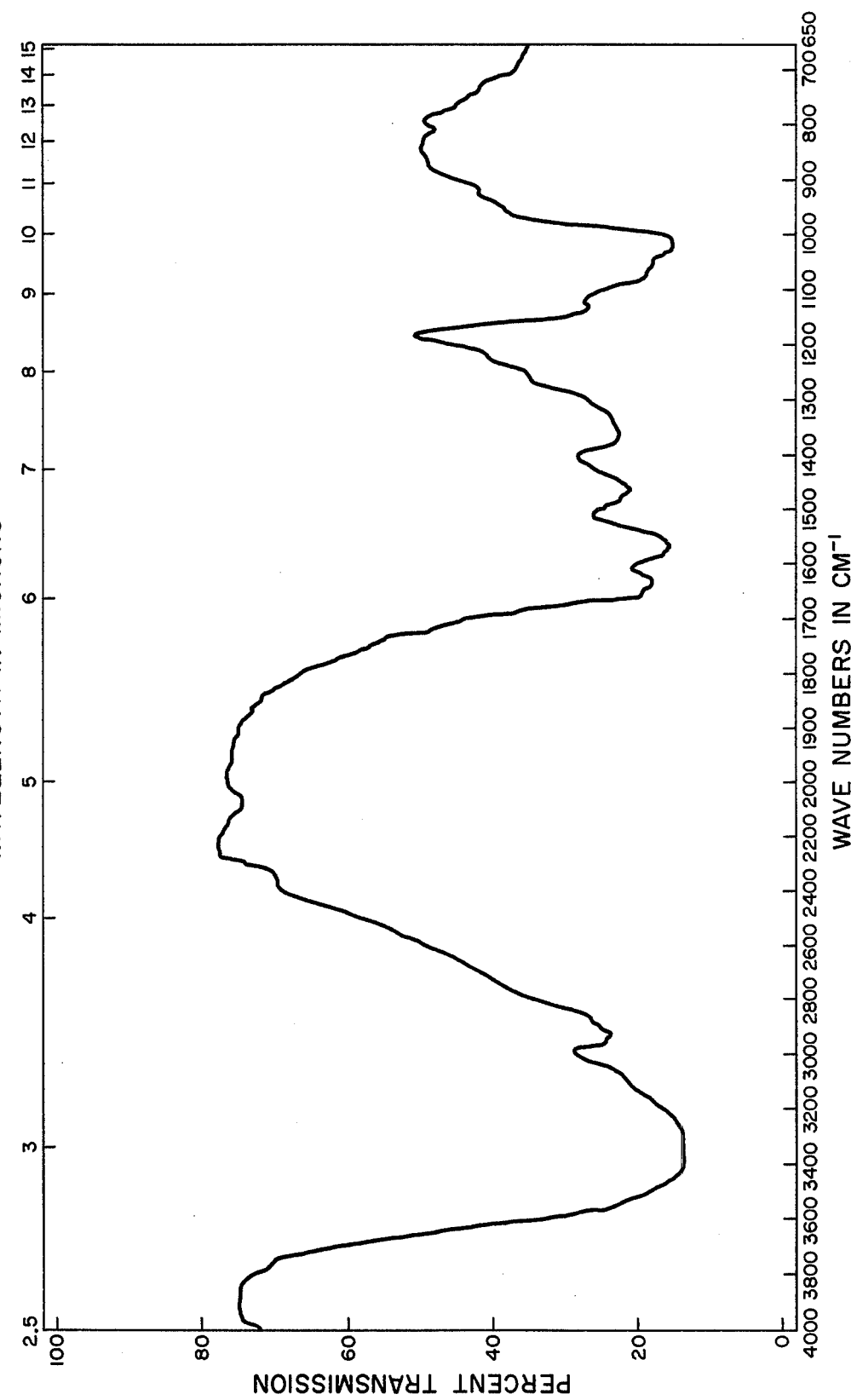

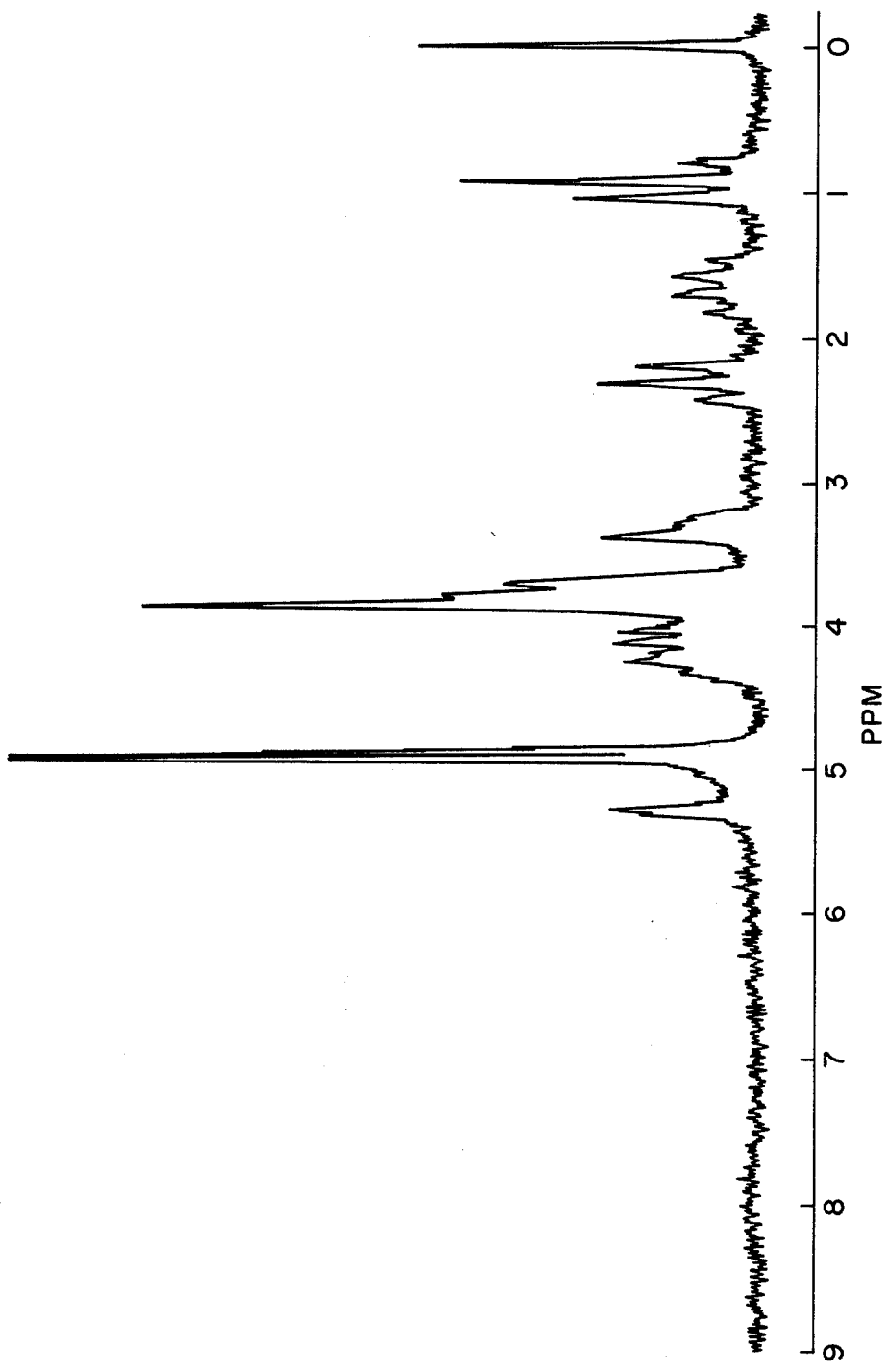
FIG. 4 NUCLEAR MAGNETIC RESONANCE SPECTRUM OF BU-2183A₂ HYDROCHLORIDE IN D₂O

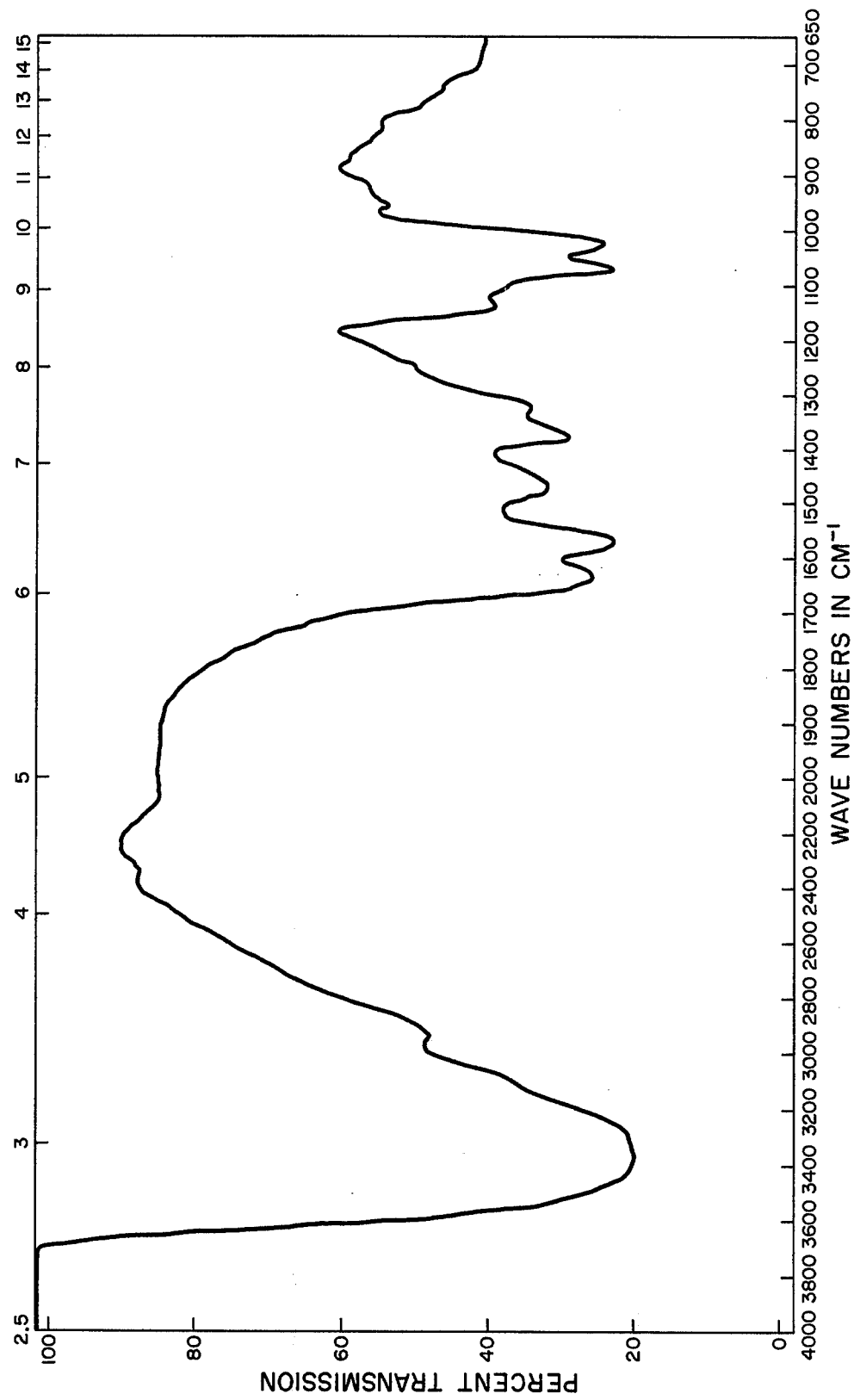

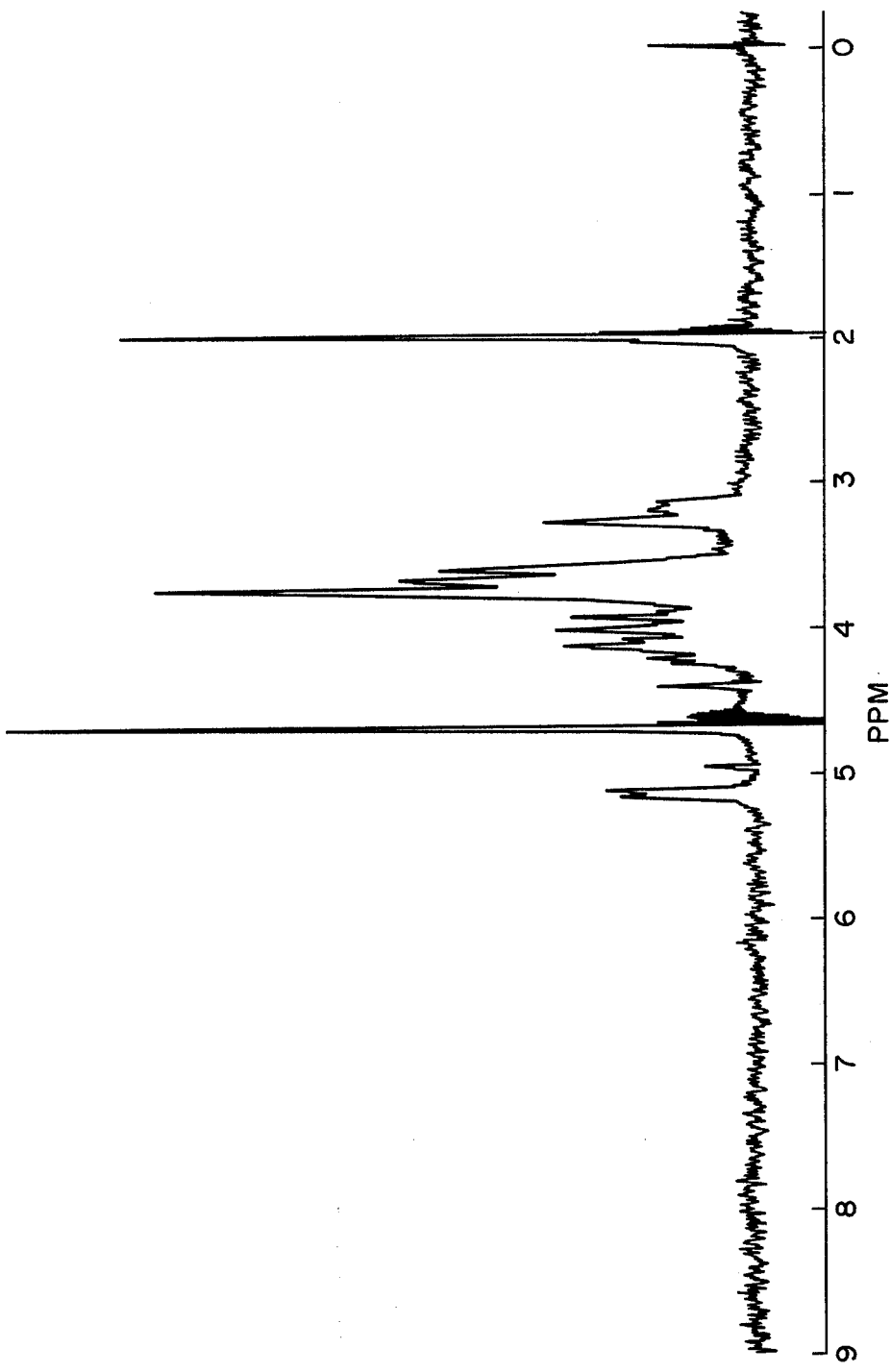
FIG. 6 NUCLEAR MAGNETIC RESONANCE SPECTRUM OF BU-2183B HYDROCHLORIDE IN $D_2O$

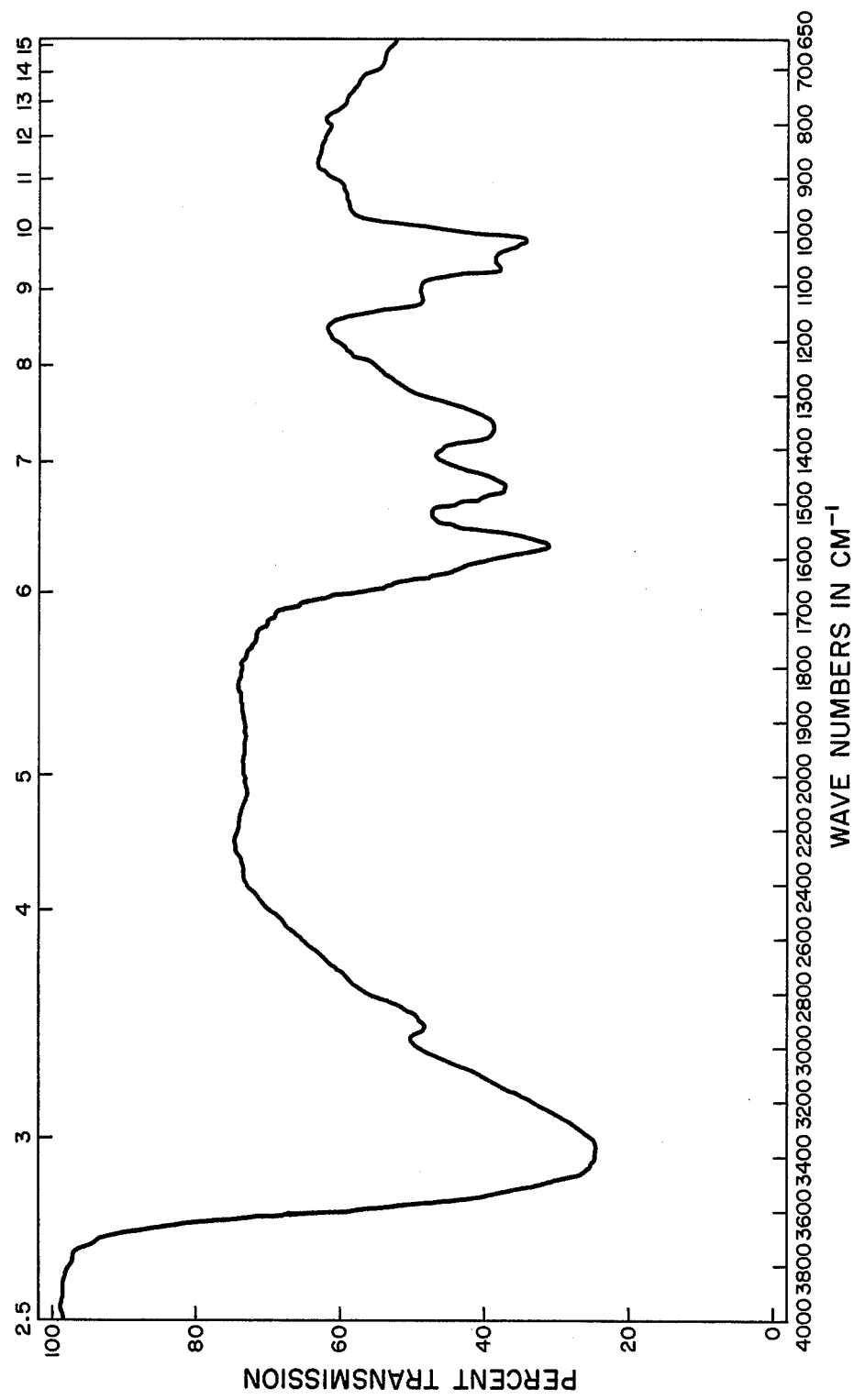

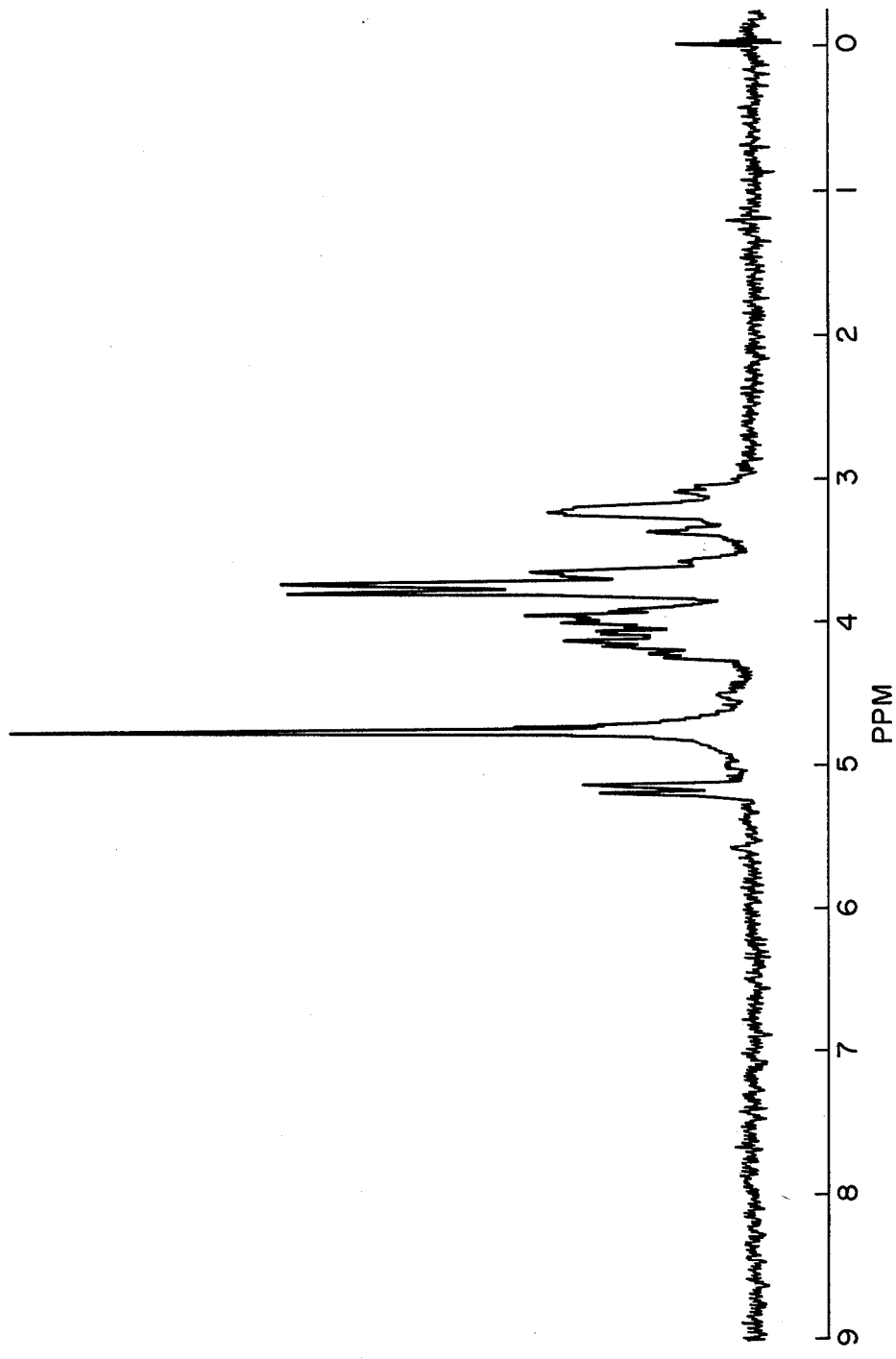
FIG. 8 NUCLEAR MAGNETIC RESONANCE SPECTRUM OF BU-2183D HYDROCHLORIDE IN $D_2O$

ANTIBIOTIC COMPLEX

CROSS-REFERENCE TO RELATED APPLICATION

This application is a divisional of co-pending U.S. application Ser. No. 627,391 filed Oct. 30, 1975, now U.S. Pat. No. 4,012,576, issued Mar. 15, 1977, which in turn is a continuation-in-part of U.S. application Ser. No. 532,137 filed Dec. 12, 1974 and now abandoned.

BACKGROUND OF THE INVENTION (1) Field of the Invention

This invention relates to new aminoglycoside antibiotic complex and to its production, recovery and separation into five components, three of which are bioactive.

(2) Description of the Prior Art

Various antibiotics are known in the art including several aminoglycoside antibiotics such as kanamycin, gentamycin, streptomycin, neomycin, tobramycin and paromomycin. There exists a need, however, for additional new broad-spectrum antibiotics, particularly those having activity against aminoglycoside-resistant organisms such as Pseudomonas.

SUMMARY OF THE INVENTION

There is provided by the present invention a new aminoglycoside antibiotic complex designated Bu-2183, said complex being prepared by cultivating a new species of Pseudomonas designated Pseudomonas sp. strain D946-B83, A.T.C.C. No. 31086, in an aqueous nutrient medium containing assimilable sources of nitrogen and carbon under submerged aerobic conditions until a substantial amount of Bu-2183 complex is produced by said organism in said culture medium and optionally recovering the Bu-2183 complex from the culture medium. The invention also provides a process for producing as separate substances the individual components of the Bu-2183 complex including especially the antibiotic components designated Bu-2183 A, $A_2$ and B and the useful intermediate designated Bu-2183D, which process comprises producing the Bu-2183 complex by the above-described method, separating the antibiotic complex from the mycelium of the culture medium, adsorbing the Bu-2183 complex on a cationic ion-exchange resin, fractionally eluting the Bu-2183 components from the adsorbent and recovering the fractions of the desired components.

DESCRIPTION OF THE DRAWINGS

FIG. 1 shows the infra-red absorption spectrum of Bu-2183 A free base when pelleted in potassium bromide.

FIG. 2 shows the proton magnetic resonance spectrum of Bu-2183 A as the hydrochloride salt dissolved in $D_2O$ using 2,2-dimethyl-2-silapentane-5-sulfonate as the internal standard as determined with a JEOL 60 MHz NMR spectrometer (type TNM-C-60HL).

FIG. 3 shows the infra-red absorption spectrum of Bu-2183 $A_2$ free base when pelleted in potassium bromide.

FIG. 4 shows the proton magnetic resonance spectrum of Bu-2183 $A_2$ as the hydrochloride salt dissolved in $D_2O$ using 2,2-dimethyl-2-silapentane-5-sulfonate as the internal standard as determined with a JEOL 60 MHz NMR spectrometer (type TNM-C-60HL).

FIG. 5 shows the infra-red absorption spectrum of Bu-2183 B free base when pelleted in potassium bromide.

FIG. 6 shows the proton magnetic resonance spectrum of Bu-2183 B as the hydrochloride salt dissolved in $D_2O$ using 2,2-dimethyl-2-silapentane-5-sulfonate as the internal standard as determined with a JEOL 60 MHz NMR spectrometer (type TNM-C-60HL).

FIG. 7 shows the infra-red absorption spectrum of Bu-2183 D free base when pelleted in potassium bromide.

FIG. 8 shows the proton magnetic resonance spectrum of Bu-2183 D as the hydrochloride salt dissolved in $D_2O$ using 2,2-dimethyl-2-silapentane-5-sulfonate as the internal standard as determined with a JEOL 60 MHz NMR spectrometer (type TNM-C-60HL).

DETAILED DESCRIPTION

This invention relates to a novel aminoglycoside antibiotic complex designated herein as Bu-2183 and to its preparation by fermentation of a new species of Pseudomonas designated Pseudomonas sp. strain D946-B83 in the Bristol-Banyu culture collection. The above organism is a psychrophilic soil bacterium which was isolated from an Indian soil sample. A culture of the organism has been deposited in the American Type Culture Collection, Washington, D.C., and added to its permanent collection of microorganisms as A.T.C.C. 31086.

The novel aminoglycoside complex of this invention comprises at least five aminoglycoside components, three of which designated Bu-2183 A, $A_2$, and B are found to be bio-active and two, designated Bu-2183 C and D, are bio-inactive.

The antibiotic complex Bu-2183 and each of the three above-mentioned bio-active antibiotic components have a broad spectrum of antibacterial activity and inhibit most of the aminoglycoside-resistant organisms including Pseudomonas species. The antibiotics Bu-2183, Bu-2183A, Bu-2183$A_2$ and Bu-2183B are valuable as antibacterial agents, as nutritional supplements in animal feeds and as therapeutic agents in poultry and animals, including man. They are valuable in the treatment of infectious diseases caused by Gram-positive and Gram-negative bacteria, particularly diseases caused by aminoglycoside-resistant organism. One of the novel bio-inactive components of the fermentation-produced complex, i.e. Bu-2183 D, is of use as an intermediate in the semi-synthetic preparation (as by N-acylation) of the bio-active components Bu-2183 A, $A_2$ and B.

The Microorganism

The Bu-2183 antibiotic producing organism designated Pseudomonas sp. strain D946-B83, A.T.C.C. 31086 is a strictly aerobic, non-sporulating and Gram-negative bacterium. The cells are rod-shaped and produce unipolar multiflagella. Strain D946-B83 is a psychrotrophic organism growing at 4° C. but not at 41° C. It produces fluorescent pigment in glutamate medium and skimmed milk solution but not in King's B medium (H. Iizuka, & K. Komagata: An Attempt At Grouping Of The Genus Pseudomonas. J. Gen. Appl. Microbiol. 9: 73–82, 1963). Cytochrome oxidases are not produced. The morphological, cultural and physiological characteristics of strain D946-B83 are described below:

Morphology

Strain D946-B83 is characterized by having motile, non-sporulating and Gram-negative rods. The cells are straight, occasionally bent along the long axis, and produce uni-polar tuft flagella. Poly-$\beta$-hydroxy butyrate is not contained as a cellular reserve (R. Y. Stanier, N. J. Palleroni & M. Doudoroff: The Aerobic Pseudomonads: A Taxonomic Study. J. Gen Microbiol. 43: 159–271, 1966). No sheath, stalk or slime is produced.

Growth Characteristics

Colony on nutrient agar and yeast extract agar: Abundant growth. 0.5–1.5 mm diameter after 1 day. Diffused, circular and somewhat raised. Smooth and soft. Opaque, whitish cream, later light buff-orange. Slightly viscous. No diffusible pigment.

Nutrient broth and yeast extract broth: Abundant growth. Turbid, later with sediment and occasionally pellicle.

Yeast extract agar stab: Growth only on surface. No growth under any anaerobic condition.

Chemically defined inorganic salts medium: Moderate growth when added with glucose or lactate as a sole carbon source.

Requirement for growth factor: None.

Growth temperature: Restricted growth at 4° C. Moderate to abundant growth at 10°–32° C. Scant growth at 37° C. No growth at 41° C.

Effect of media pH: No growth at pH 4.0. Restricted growth at pH 4.5 and pH 10.5–11.0. Moderate to good growth at pH 5.5–9.5.

NaCl effect: No growth at 12% NaCl. Restricted growth at 6–9%. Moderate growth at 5% or less.

The above-described morphological and cultural characteristics are similar to those of the family Pseudomonadaceae.

Physiological Characteristics

Strain D946-B83 produces diffusible fluorescent pigment in certain media but not in others while a known species of Pseudomonas, i.e. *Pseudomonas fluorescens,* shows abundant fluorescence production (Table 1).

The physiological and biochemical characteristics of strain D946-B83 are shown in Table 2. Utilization of carbohydrate and other carbon sources by the organism is shown in Table 3 comparatively with those of two known Pseudomonal species, i.e. *Ps. fluorescens* and *Ps. aeruginosa.*

Taxonomy

Strain D946-B83 appears to belong to the pseudomonads group in view of the above-described morphological, cultural and physiological characteristics. According to the taxonomic system proposed by Stanier et al. (R. Y. Stanier, N. J. Palleroni and M. Doudoroff: The Aerobic Pseudomonads: A Taxonomic Study. J. Gen. Microbiol. 43: 159–271, 1966) for the aerobic pseudomonads, strain D946-B83 is rather closely related to *Pseudomonas fluorescens* except for its negative egg-yolk reaction, negative utilization of inositol and negative oxidase production. Among the 13 type species of aerobic pseudomonads examined by Stanier, only *Pseudomonas maltophilia* is reported to show negative oxidase reaction. This organism, however, is quite different from strain D946-B83 in the lack of fluorescent pigment, positive methionine requirement, absence of growth at 4° C., negative arginine dihydrolase and different substrate utilization. Thus, strain D946-B83 is considered to belong to a new species of the genus Pseudomonas.

Preparation of the Antibiotics

Antibiotic complex Bu-2183 is produced by cultivating the novel Pseudomonas species designated Pseudomonas sp. strain D946-B83, A.T.C.C. 31086, under submerged aerobic conditions in an aqueous nutrient medium. The organism is grown in a nutrient medium containing an assimilable carbon source, for example an assimilable carbohydrate. Examples of preferred carbon sources include glucose, fructose, mannose, glycerol and the like. The nutrient medium should also contain an assimilable nitrogen source such as, for example, fish meal, soybean meal, peptones, etc. Nutrient inorganic salts may also be incorporated in the culture medium, and such salts may comprise any of the usual salts capable of providing sodium, potassium, ammonium, calcium, phosphate, sulfate, chloride, bromide, nitrate, carbonate or like ions.

Production of the Bu-2183 complex can be effected at any temperature conducive to satisfactory growth of the organism, e.g. 10°–32° C., and is most preferably carried out at a temperature of around 28°–30° C. Ordinarily optimum production is obtained in 3–5 days. The optimum pH range of the medium is found to be about pH 5.5–9.5 and, most advantageously, the medium is adjusted to a pH of about 7. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium.

A preferred procedure for preparing the Bu-2183 antibiotic complex is as follows:

A well-grown agar slant of Pseudomonas strain D946-B83 was used to inoculate seed medium containing 3% glucose, 2% fish meal, 0.5% soybean meal, 0.2% peptone and 0.6% $CaCO_3$, the pH being adjusted to 7.0 before sterilization. The seed culture was incubated at 28° C. for 48 hours on a rotary shaker (250 rpm), and 2 ml. of the growth was transferred to 100 ml. of the fermentation medium in a 500 ml. Erlenmeyer flask which contained 2% glycerol, 2% linseed meal, 1% peanut meal, 2% fish meal, 0.3% $(NH_4)_2SO_4$ and 0.5% $CaCO_3$. Antibiotic production reached a maximum after 3 to 5 days shaking at 28° C. The antibiotic activity in the fermentation broth was determined by a paper disc-agar diffusion assay using *Bacillus subtilis* PCI 219 as the test organism. Strain D946-B83 produced 1,500 to 2,000 mcg./ml. of the antibiotic complex by the shake flask fermentation method.

After optimum broth potency has been obtained (as determined for example by the assay procedure mentioned above), the broth is adjusted to a pH of about 2 whereby the basic water-soluble antibiotic complex is separated from the mycelium and dissolved in the aqueous fermentation medium. The broth is then filtered, preferably with filter aid, and the filtrate containing the antibiotic neutralized to a pH of about 7. The neutralized filtrate is passed through a cationic ion-exchange resin, preferably of the IRC-50 Amberlite type in the ammonium form. The resin is then washed with water and dilute (N/50) $NH_4OH$ and the antibiotic complex eluted from the resin with a suitable eluant, e.g. N/2 $NH_4OH$. The active eluants are combined, concentrated in vacuo and evaporated or lyophilized to obtain the crude Bu-2183 antibiotic complex.

The crude solid thus obtained was shown by TLC to contain at least three active components which have been designated herein as Bu-2183 A, $A_2$ and B as well as at least two inactive components which have been designated herein as Bu-2183 C and D. The Bu-2183 complex may be separated into its components Bu-2183 A, $A_2$, B, C and D by use of a cationic ion-exchange resin, preferably a resin of the Amberlite CG-50 type in the ammonium form. The complex after being dissolved in water is applied to the resin, washed with water and dilute (N/40) ammonium hydroxide and eluted with a suitable eluant. Ammonium hydroxide (N/20) has been found to allow separation of components Bu-2183 A and B. Further elution of the column with a more concentrated ammonium hydroxide solution, e.g. (N/10), gives Bu-2183 C and D which are ninhydrin-positive but bioinactive. To obtain purified component Bu-2183 $A_2$, it is usually necessary to perform additional column chromatography on the Bu-2183 A fraction to separate the components Bu-2183 $A_2$ and Bu-2183 A. Complete separation and purification of each component is achieved by repeating the chromatographic separation procedure described above. As shown below in Table 4, two TLC systems designated herein as S-117 and S-122 were found to be suitable to differentiate the four components Bu-2183 A, B, C and D. During the chromatographic purification of component Bu-2183 A as described in detail in the examples which follow, a further bio-active aminoglycoside component was found which is designated herein as Bu-2183 $A_2$. Component Bu-2183 $A_2$ may be differentiated from component Bu-2183 A by the TLC systems S-117 and S-122 as shown below in Table 5.

Characterization Data for Bu-2183 Antibiotic Components

Bu-2183 A

The antibiotic substance Bu-2183 A is a white amorphous base which is soluble in water, slightly soluble in methanol and ethanol and practically insoluble in n-butanol, acetone and other common organic solvents.

Antibiotic Bu-2183 A is capable of forming salts with acids, and pharmaceutically acceptable acid addition salts of the antibiotic are included within the present invention. Examples of suitable pharmaceutically acceptable acid addition salts include the non-toxic salts with organic and inorganic acids such as for example hydrochloric, sulfuric, phosphoric, acetic, stearic, propionic, tartaric, maleic, benzoic, succinic and the like.

Component Bu-2183 A gives positive reactions with ninhydrin and anthrone reagents but negative reactions with Tollens, Fehling and Sakaguchi reagents.

The specific rotation of Bu-2183 A base is $[\alpha]_D^{21} = +78.5°$ (c, 1.0, water).

A sample of component Bu-2183 A when precipitated from ethanol analyzed as $C_{15}H_{31}N_3O_9 \cdot C_2H_5OH \cdot H_2O$.

Anal. Calc'd.: C, 44.24; H, 8.52; N, 9.11; O, 38.13. Found: C, 44.25; H, 8.08; N, 9.11; O(by difference), 38.56.

The di-N-acetate of Bu-2183 A was obtained as colorless needles, m.p. 149°-150° C. It has a molecular weight of 481 as determined by osmometry and analyzed as $C_{19}H_{35}N_3O_{11} \cdot H_2O$.

Anal. Calc'd.: C, 45.68; H, 7.47; N, 8.41; O, 38.44. Found: C, 45.73; H, 7.49; N, 8.19; O(by difference), 38.59.

Bu-2183 A is weakly basic and has titratable groups having $pK_a'$ values of 6.90 and 9.40 in water. The approximate molecular weight of the antibiotic as calculated from titration data is 398.

Component Bu-2183 A exhibits only end absorption of ultraviolet light. When pelleted in potassium bromide, it has an infrared spectrum substantially as shown in FIG. 1 with characteristic absorption bands at the following wave numbers in $cm^{-1}$: 1635 and 1570 (amide) and 1080 and 1020 (hydroxyl groups). When dissolved in deuterium oxide at a concentration of about 8%, the NMR spectrum of Bu-2183 A hydrochloride salt is substantially as shown in FIG. 2. The spectrum shows an anomeric proton at $\delta 5.17$ ppm (1H, d, J = 3 Hz) and a propionyl group at $\delta 1.12$ (3H, t, J = 7.5 Hz) and 2.29 (2H, q, J = 7.5 Hz) ppm.

The structure of Bu-2183 A has been determined to be

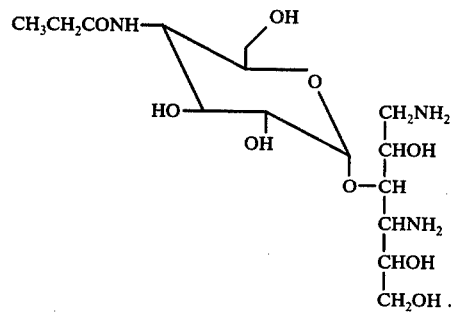

Bu-2183 $A_2$

Antibiotic component Bu-2183 $A_2$ like Bu-2183 A above is a white amorphous base which is soluble in water, slightly soluble in methanol and ethanol and practically insoluble in n-butanol, acetone and other common organic solvents. It is capable of forming salts with acids, and pharmaceutically acceptable acid addition salts of the Bu-2183 base are included within the present invention. Component Bu-2183 $A_2$ gives positive ninhydrin and anthrone reactions and negative Tollens, Fehling and Sakaguchi reactions.

The specific rotation of Bu-2183 $A_2$ base is $[\alpha]_D^{25} = +79.1°$(c, 0.43, $H_2O$).

A sample of Bu-2183 $A_2$ isolated on the carbonate salt analyzed as $C_{16}H_{33}N_3O_9 \cdot \frac{1}{2} H_2CO_3$.

Anal. Calc'd.: C, 44.79; H, 7.75; N, 9.50; O, 37.96. Found: C, 44.35; H, 7.83; N, 9.21; O(by difference), 38.61.

Component Bu-2183 $A_2$ exhibits only end absorption of ultraviolet light. When pelleted in KBr, it has an infrared spectrum substantially as shown in FIG. 3. When dissolved in $D_2O$ at a concentration of about 6%, the NMR spectrum of Bu-2183 $A_2$ hydrochloride salt is substantially as shown in FIG. 4. Component Bu-2183 $A_2$ may be distinguished from Bu-2183 A and Bu-2183 B by the presence of an n-butyryl group in the NMR spectrum at $\delta 0.92$ (3H, t), 1.63 (2H, sixtet) and 2.30 (2H, t) ppm in place of the propionyl or acetyl group in components A & B.

The structure of component Bu-2183 $A_2$ has been determined to be

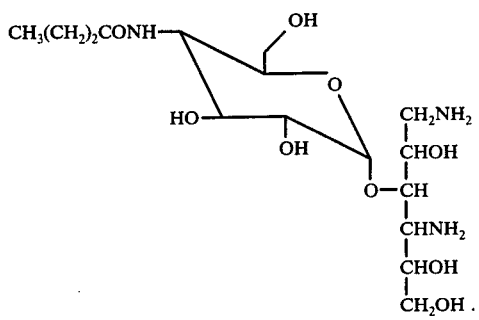

Bu-2183 B

The antibiotic Bu-2183 B is very similar in appearance and solubility to components Bu-2183 A and $A_2$, being a white amorphous base which is soluble in water, slightly soluble in methanol and ethanol and practically insoluble in n-butanol, acetone and other common organic solvents.

Antibiotic Bu-2183 B is capable of forming salts with acids, and pharmaceutically acceptable acid addition salts of the antibiotic are included within the present invention.

Component Bu-2183 B gives positive reactions with ninhydrin and anthrone reagents but negative reactions with Tollens, Fehling and Sakaguchi reagents.

The specific rotation of Bu-2183 B base is $[\alpha]_D^{21} = + 85°$ (c, 1.0, water).

A sample of component Bu-2183 B when precipitated from ethanol analyzed as $C_{14}H_{29}N_3O_9 \cdot C_2H_5OH \cdot H_2O$.

Anal. Calc'd.: C, 42.95; H, 8.34; N, 9.36; O, 39.35. Found: C, 42.69; H, 7.78; N, 8.86; O(by difference), 40.67.

The di-N-acetate of Bu-2183 B was obtained as colorless prisms, m.p. 159°–162° C. It has a molecular weight of 484 as determined by osmometry and analyzed as $C_{18}H_{33}N_3O_{11} \cdot H_2O$.

Anal. Calc'd: C, 44.53; H, 7.27; N, 8.66; O, 39.54. Found: C, 44.96; H, 7.44; N, 8.52; O(by difference), 39.08.

Bu-2183 B is weakly basic and has titratable groups having $pK_a'$ values of 7.15 and 9.35 in water. The approximate molecular weight of the antibiotic as calculated from titration data is 409.

Component Bu-2183 B exhibits only end absorption of ultraviolet light. When pelleted in potassium bromide, it has an infrared spectrum substantially as shown in FIG. 5 with characteristic absorption bands at the following wave numbers in cm$^{-1}$: 1635 and 1570 (amide) and 1080 and 1020 (hydroxyl groups). When dissolved in deuterium oxide at a concentration of 10%, the NMR spectrum of Bu-2183 B hydrochloride salt is substantially as shown in FIG. 6. The NMR spectrum shows that Bu-2183 B may be distinguished from Bu-2183 A and $A_2$ by the presence of an acetyl group at $\delta 2.02$ ppm (3H, s,) instead of the propionyl or n-butyryl group as in A and $A_2$, respectively.

Component Bu-2183 B has the structure

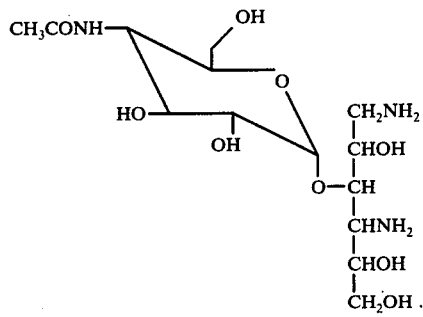

Characterization Data For Intermediate Bu-2183 D

The bio-inactive component Bu-2183 D is a white amorphous base which is soluble in water, slightly soluble in methanol and ethanol, and practically insoluble in n-butanol, acetone and other common organic solvents.

Compound Bu-2183 D is capable of forming salts with acids and such acid addition salts of the base are included within the present invention.

Component Bu-2183 D gives positive reactions with ninhydrin and anthrone reagents but negative reactions with Tollens, Fehling and Sakaguchi reagents.

The specific rotation of Bu-2183 D base is $[\alpha]_D^{21} = + 72.5°$ (c, 1.0, water).

A sample of component Bu-2183 D isolated as the carbonate salt analyzed as $C_{12}H_{27}N_3O_8 \cdot H_2CO_3$.

Anal. Calc'd.: C, 38.70; H, 7.25; N, 10.42; O, 43.63. Found: C, 38.86; H, 6.93; N, 10.14; O (by difference), 44.07.

Bu-2183 D is weakly basic and has three titratable groups with $pK\alpha'$ values of 6.95 (2 equivalents) and 9.68 in water.

The tri-N-acetate of Bu-2183 D was obtained as colorless prisms, m.p. 159°–162° C. This salt was determined to be identical with the di-N-acetate of Bu-2183 B.

Component Bu-2183 D exhibits only end absorption of ultraviolet light. When pelleted in potassium bromide, it has an infrared spectrum substantially as shown in FIG. 7. The spectrum indicates the lack of the amide carbonyl bands which are present in the bioactive components Bu-2183 A, $A_2$ and B. When dissolved in deuterium oxide at a concentration of 10%, the NMR spectrum of Bu-2183 D hydrochloride salt is substantially as shown in FIG. 8. The structure of Bu-2183 D has been determined to be

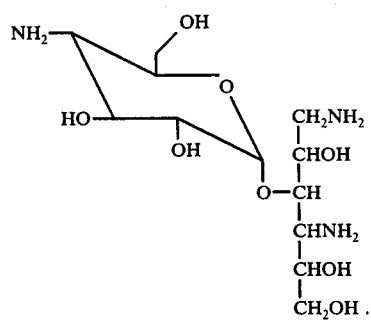

Structure Determination of Bu-2183 Components

Mild acidic hydrolysis of Bu-2183 A and B (1N HCl/MeOH, 80° C., 3 hours) gave the same desacyl compound, $C_{12}H_{27}N_3O_8$, which was identical with component Bu-2183 D obtained by chromatographic separation of the crude Bu-2183 complex. Total N-acetylation of Bu-2183 D gave tri-N-acetate, $C_{18}H_{33}N_3O_{11}$, which was identified as the di-N-acetate of component Bu-2183 B.

Acid hydrolysis of Bu-2183 B in methanolic hydrogen chloride (saturated, refluxing temperature, 24 hours) yielded an aglycone and an amino sugar along with component Bu-2183 D. The aglycone was isolated as the crystalline sulfate, mp 263°–264° C, which analyzed for $C_6H_{16}N_2O_4 \cdot H_2SO_4$.

Anal. Calc'd.: C, 25.90; H, 6.52; N, 10.07; S, 11.52. Found: C, 26.10, H, 6.47, N, 9.93, S, 11.29.

The 220 $MH_z$ NMR spectrum of its N,O-hexaacetate along with mass spectral data obtained with the N-acetyl-O-TMS, N-acetyl-diisopropylidene and hexa-N,O-acetyl derivatives of the aglycone suggested a 1,4-diamino-2, 3, 5, 6-tetra-ol structure for the aglycone part.

The di-N-acetate of the aglycone was obtained as colorless needles, mp 114°–115° C., and analyzed for $C_{10}H_{20}N_2O_6$.

Anal. Calc'd.: C, 45.45; H, 7.63; N, 10.60. Found: C, 45.37; H, 7.97; N, 10.57.

Since the D-glucose-type configuration was thought to be most probable for the aglycone, the preparation of 1, 4-diamino-1, 4-dideoxy-D-sorbitol from 4-amino-4-deoxy-D-glucose was carried out and the product was shown to be the aglycone by TLC and NMR analysis.

The amino sugar part obtained after the above acidic methanolysis of component B was purified by Amberlite CG-50 chromatography and separated into α and β forms of methylglycoside, the α-form being the major product. N-Acetylation of the α-methylglycoside yielded colorless prisms, mp 185°–186° C. which analyzed for $C_9H_{17}NO_6$.

Anal. Calc'd: C, 45.95; H, 7.28; N, 5.95. Found: C, 45.93; H, 7.43; N, 5.88.

The mass spectrum of this N-acetyl derivative showed a peak at m/e 204 (M -31) attributable to the loss of a glycosidic methoxyl group from the molecule. Thus, the free amino sugar should have the formula of $C_6H_{13}NO_5$.

The α and β forms of methylglycoside were identified as methyl 4-amino-4-deoxy-α- and β-D-glucopyranoside, respectively, by the IR and NMR spectra of their tetra-N,O-acetyl derivatives. The IR spectra of authentic specimens of these sugars isolated from 4-trehalosamine (J. Antibiotics, 27, 145, 1974) were in agreement with the IR spectra of the experimental samples.

Acid hydrolysis of Bu-2183 D in 6N HCl (reflux, 3 hours) gave the same aglycone and amino sugar as those isolated from the hydrolyzate of Bu-2183 B.

Bu-2183 C obtained by chromatographic separation of the crude Bu-2183 complex was hydrolyzed in methanol containing 1N HCl at refluxing temperature for 3 hours. The aglycone part was identical with that of the other components of Bu-2183 and the sugar portion was identified as methyl D-glucoside by TLC, NMR and gas chromatography. Accordingly, the molecular formula for Bu-2183 C is $C_{12}H_{26}N_2O_9$.

Based on the above data the structures of the Bu-2183 components were determined to be as follows:

| Bu-2183 Component | R |
|---|---|
| A | $C_2H_5CONH-$ |
| B | $CH_3CONH-$ |
| $A_2$ | $n-C_3H_7CONH-$ |
| C | $HO-$ |
| D | $NH_2-$ |

Antimicrobial Activity

In vitro tests indicate that the complex Bu-2183 and the individual antibiotic components Bu-2183 A, $A_2$ and B have a broad spectrum of antibacterial activity. The antibiotic complex and active components are particularly useful in inhibiting most aminoglycoside-resistant organisms. Component Bu-2183 $A_2$ is found to be more active than Bu-2183 B but less active than Bu-2183 A.

The minimum inhibitory concentrations (MIC) of Bu-2183 A and B were determined against a wide variety of bacteria by the two-fold agar dilution method on Nutrient Agar plates. The inocula-replicating device of Steers et al. was used. Inoculum size was adjusted to be $10^4$ dilution of overnight culture of the test organisms in Heart Infusion Broth (Difco). The results are shown in Table 6 along with those of kanamycin which was comparatively tested as a reference antibiotic.

The intrinsic activities of Bu-2183 A and B are moderate or rather weak in terms of MIC values, the component A being about 2–4 fold more active than B. However, they exhibit a broad spectrum of antibacterial activity against Gram-positive and Gram-negative bacteria including many of the aminoglycoside-resistant organisms and Pseudomonas strains.

Table 7 below shows minimum inhibitory concentrations of components Bu-2183 A and $A_2$ against several pathogenic organisms.

A sample of Bu-2183 complex of approximately 30–40% purity was found to inhibit *E. coli* A20365 at a concentration of 12.5 mcg./ml., *K. pneumoniae* D-11 at a concentration of 12.5 mcg./ml., and *Ps. aeruginosa* A9930 at a concentration of 25 mcg./ml.

Effect Of Media pH On MIC

Effect of media pH on the MIC of Bu-2183 A was studied by two-fold agar dilution method using Nutrient Agar Medium at pH 6.0, 7.0, 8.0 and 9.0. The results shown in Table 8 indicated that the activity of Bu-2183 A increased at alkaline pH and decreased at acidic pH.

Effect Of Media

The effect of media on the activity of Bu-2183 A and B was determined against 8 test organisms. The media tested were Nutrient Agar, Heart Infusion Agar and Mueller-Hinton Agar. The media pH was adjusted at pH 8. As shown in Table 9, the greatest in vitro activity was demonstrated when Nutrient Agar was used as the test medium.

In Vivo Activity And Toxicity

Bu-2183 A and B were evaluated in vivo in experimental infections of mice. The pathogenic bacteria employed were S. aureus Smith, E. coli NIHJ and Ps. acruginosa A9930. Mice were challenged with a 100 × $LD_{50}$ dose of the pathogens in a 5% suspension of hog gastric mucin. A single subcutaneous treatment with the antibiotic was made immediately after the bacterial challenge (0 hour), and in a double dose schedule the antibiotic was administered at 0 and 3 hours after the challenge. Groups of 5 mice were used for each dosage level and the animals were observed for 5 days to determine the median protective dose ($PD_{50}$).

The results are shown in Table 10. Bu-2183 A and B afforded in vivo activity against all three of the infections tested.

The acute toxicity of Bu-2183 A and B was determined in mice by the subcutaneous and intravenous routes. The mice were observed for 15 days and the intravenous (i.v.) and subcutaneous (s.c.) $LD_{50}$'s of component Bu-2183 A were found to be 2500 mg./kg. and 1000 mg./kg., respectively. Component Bu-2183 B was much less toxic than Bu-2183 A and no death occurred at doses up to 2000 mg./kg. by either i.v. or s.c. routes during the observation period of 15 days.

Utility Of Component Bu-2183 D

Component Bu-2183 D while bio-inactive is a valuable intermediate in the semi-synthetic preparation of the bio-active components Bu-2183 A, $A_2$ and B. Thus, the free amino group of intermediate Bu-2183 D (after suitable protection of other reactive functional groups) may be N-acylated according to methods known per se to produce (after removal of any protecting groups) the N-butyryl derivative Bu-2138A, the N-acetyl derivative Bu-2183B or the N-propionyl derivative Bu-2183$A_2$.

Table 1

| | Production Of Fluorescent Pigment | |
|---|---|---|
| Medium | Bu-2183 Producer D946 - B83 | Ps. Fluorescens NIHJ B254 |
| Yeast extract agar | − | + |
| King's B medium | −∼± | ++ |
| 20% Skimmed milk solution | ++ | ++ |
| Glutamate broth | ++ | ++ |

Table 2

Physiological And Biological Characteristics Of Strain D946-B83

| Test | Response | Method & Medium Employed |
|---|---|---|
| Arginine dihydrolase | Positive | Modified method of Stanier et al[1] |
| Catalase | Positive | Hydrogen peroxide on the colony |
| Oxidase (cytochrome oxidase) | Negative | Tested by three different methods[1,4] |
| Extracellular hydrolases | | |
| Gelatin hydrolase | Positive | Method of Stanier et al[1] |
| Starch hydrolase | Negative | Method of Stanier et al[1] |
| Voges-Proscauer reaction | Negative | Peptone broth plus 1% glucose |
| Indole production | Negative | Peptone broth (Kovac's reagent) |
| $H_2S$ production from cysteine and thiosulfate | Negative | Ammonium-inorganic salts plus cysteine and thiosulfate Lead acetate paper for detection of $H_2S$ |
| Gelatin liquefaction | Positive (rapidly liquefied) | Peptone broth plus 25% gelatin[5] |
| Reactions in skimmed milk solution | Greenish yellow fluorescent pigment produced. Peptonized. pH alkalized | 20% skimmed milk solution sterilized by mild autoclaving (0.5 kg./cm² for 5 minutes) |
| Utilization of nitrate-N | Positive | Rhodes' inorganic salts-glycerol-nitrate medium[2] |
| Nitrite production from nitrate | Positive | Rhodes' inorganic salts-glycerol-nitrate medium[2] |
| | Negative | Peptone broth plus 0.1% $KNO_3$ |
| Utilization of ammonium-N | Positive | Koser's citrate medium |
| Ammonia production from peptone | Positive | Peptone broth (Nessler's reagent) |
| Denitrification | Negative | Method of Stanier et al[1] |
| Gas from carbohydrate | Negative | Nutrient broth plus 1% glucose |
| Utilization of urea | Positive | Christensen's urea medium |
| Utilization of citrate | Positive | Simmon's citrate medium and Koser's citrate medium |
| Utilization of oxalate | Negative | Oxalate instead of citrate in Simmon's and Koser's media |
| Egg-yolk reaction | Negative | Method employed by Stanier et al[1] |
| Cleavage mechanism of aromatic compound | Ortho-cleavage | Modified method of Stanier et al[1] |
| Production of phenazine pigments including pyocyanin, chloraphine and phenazine α-carboxylic acid | Negative | King's A medium |

[1] R. Y. Stanier, N. J. Palleroni & M. Doudoroff: The Aerobic Pseudomonads: A Taxonomic Study. J. Gen. Microbiol. 43: 159-271, 1966
[2] M. E. Rhodes:The Characterization of Pseudomonas Fluorescens. J. Gen. Microbiol. 21: 221-263, 1959
[3] H. Iizuka & K. Komagata: An Attempt At Grouping Of The Genus Pseudomonas, J. Gen Appl. Microbiol. 9: 73-82, 1963
[4] H. Iizuka & K. Komagata: Taxonomy Of Genus Pseudomonas With Special Reference To Their Modes Of Metabolism Of Carbon Compounds. J. Gen. Appl. Microbiol. 9: 83-95, 1963
[5] V. B. D. Skerman: Abstracts Of Microbiological Methods. Wiley-Interscience, New York, London, Sydney and Toronto, P. 364, 1969

Table 3

| | Utilization Of Carbon Sources | | |
|---|---|---|---|
| Substrate | Strain D946-B83 | Ps. fluorescens NIHJ B254 | Ps. aeruginosa ATCC 19660 |
| Glycerol | + | + | + |
| L-Arabinose | + | + | − |
| D-Xylose | + | + | − |
| L-Rhamnose | − | − | − |

Table 3-continued

Utilization Of Carbon Sources

| Substrate | Strain D946-B83 | Ps. fluorescens NIHJ B254 | Ps. aeruginosa ATCC 19660 |
|---|---|---|---|
| D-Fructose | + | + | + |
| D-Galactose | + | + | − |
| D-Glucose | + | + | + |
| D-Mannose | + | + | − |
| D-Fucose | − | − | − |
| Trehalose | + | + | − |
| Cellobiose | − | − | − |
| Maltose | − | − | − |
| Sucrose | − | − | − |
| Lactose | − | − | − |
| Raffinose | − | − | − |
| Inositol | − | + | − |
| D-Mannitol | + | + | + |
| D-Sorbitol | + | + | − |
| Dulcitol | − | − | − |
| Geraniol | − | − | + |
| Starch | − | − | − |
| Cellulose | − | − | − |
| Inulin | − | − | − |
| Salicin | − | − | − |
| Acetate | + | + | + |
| Propionate | + | + | + |
| β-OH-butyrate | + | + | + |
| 2-Ketogluconate | + | + | + |
| Succinate | + | + | + |
| Maleate | − | − | − |
| Glycollate | − | − | − |
| DL-Lactate | + | + | + |
| Pelargonate | + | + | + |
| Adipate | − | − | − |
| p-OH-benzoate | + | + | + |
| m-OH-benzoate | − | − | − |
| Methanol | − | − | + |
| Ethanol | − | − | + |
| n-Propanol | − | − | + |
| Phenol | − | − | − |
| Cresol | − | − | + |
| Monoethanolamine | − | − | − |
| Monoethylamine | − | − | − |
| Diethylamine | − | − | − |
| Triethylamine | − | − | − |
| Testosterone | − | − | − |
| Acetamide | − | − | + |
| Arginine | + | + | + |
| Valine | + | + | + |
| Norleucine | − | − | − |
| D-Tryptophan | − | − | − |
| δ-Aminovalerate | + | − | + |
| Betaine | + | + | + |
| Putrescine | + | + | + |

Basal medium contains per liter: 40 ml. of 1M-phosphate buffer (pH 6.8); 1 g., $(NH_4)_2SO_4$; 20 ml. of Hutner's vitamin-free mineral salts solution.

Table 4

TLC Of Bu-2183 Components

| System | Plate | Solvent System | Rf* A | B | C | D |
|---|---|---|---|---|---|---|
| S-117 | silica gel | $CHCl_3$—$CH_3OH$—28%$NH_4OH$ (1:3:2) | 0.39 | 0.30 | 0.21 | 0.23 |
| S-122 | silica gel | $CHCl_3$—$CH_3OH$—2N $NH_4OH$—$CH_3COOH$ (20:65:40:5) | 0.38 | 0.27 | 0.15 | 0.03 |

Table 5

TLC Of Bu-2183 Components A & A₂

| System | Plate | Solvent System | Rf* A | A₂ |
|---|---|---|---|---|
| S-117 | silica gel | $CHCl_3$—$CH_3OH$—28%$NH_4OH$ (1:3:2) | 0.49 | 0.57 |
| S-122 | silica gel | $CHCl_3$—$CH_3OH$—2N $NH_4OH$—$CH_3COOH$ (20:65:40:5) | 0.39 | 0.48 |

*detection: ninhydrin reagent

Table 6

Antibacterial Spectra Of Bu-2183 A And B

| Code # | Test Organism | MIC (mcg/ml.) Bu-2183 A | Bu-2183 B | Kanamycin A |
|---|---|---|---|---|
| Sa-2 | S. aureus Smith | 12.5 | 50 | 0.2 |
| Sa-3 | S. aureus D193 | 25 | 25 | 0.4 |
| Sa-4 | S. aureus D133 | 25 | >100 | 0.8 |
| Sa-9 | S. aureus D137 | 100 | >100 | 1.6 |
| Sa-10 | S. aureus A20239 | 25 | 100 | 25 |
| Ec-1 | E. coli NIHJ | 12.5 | 50 | 0.8 |
| Ec-2 | E. coli PO 1495 | 25 | 50 | 0.4 |
| Ec-5 | E. Coli ML 1630 | 12.5 | 50 | 100 |
| Ec-9 | E. coli NR 79/W677 | 25 | 100 | 25 |
| Ec-10 | E. coli JR 35/C600 | 6.3 | 12.5 | 12.5 |
| Ec-49 | E. coli A20107 | 12.5 | 50 | 25 |
| Ec-53 | E. coli JR 66/W677 | 6.3 | 25 | 25 |
| Ec-55 | E. coli R 5 | 25 | 100 | 6.3 |
| Ec-62 | E. coli A20895 | 12.5 | 50 | 0.8 |
| Ec-72 | E. coli A20732 | 12.5 | 25 | 12.5 |
| El-2 | Ent. cloacae A20364 | 25 | 50 | 100 |
| El-12 | Ent. cloacae A21006 | 25 | 100 | 50 |
| Pv-1 | Pr. vulgaris A9436 | 12.5 | 50 | 0.2 |
| Pg-2 | Pr. morganii A20031 | 25 | 50 | 0.8 |
| Pm-1 | Pr. mirabilis A9554 | 12.5 | 25 | 0.4 |
| Ps-2 | Prov. stuartii A20894 | >100 | >100 | 0.8 |
| Kp-1 | K. pneumoniae D11 | 3.1 | 12.5 | 0.2 |
| Kp-8 | K. pneumoniae Type 22-3038 | 25 | 100 | 100 |
| Sm-1 | Ser. marcescens A20019 | >100 | >100 | 0.8 |
| Sm-16 | Ser. marcescens A21247 | 100 | >100 | >100 |
| Pa-3 | Ps. aeruginosa A9930 | 12.5 | 25 | 6.3 |
| Pa-12 | Ps. aeruginosa A20653 | 25 | 100 | >100 |
| Pa-16 | Ps. aeruginosa # 130 | 25 | 100 | 25 |
| Pa-21 | Ps. aeroginosa A20601 | 25 | 50 | 12.5 |
| Pa-24 | Ps. aeruginosa A20896 | 25 | 100 | >100 |
| Pa-27 | Ps. aeruginosa GN 315 | 25 | 50 | 100 |
| Px-10 | Pseudomonas sp. A20621 | >100 | >100 | 12.5 |

Table 7
Antibacterial Spectra Of Bu-2183 A and A₂

| Code # | Test Organism | MIC (mcg/ml.) Bu-2183 A | Bu-2183 A$_2$ |
|---|---|---|---|
| Sa-2 | S. aureus Smith | 25 | 25 |
| Sa-3 | S. aureus D193 | 25 | 50 |
| Sa-4 | S. aureus D133 | 50 | 100 |
| Sa-9 | S. aureus D137 | 50 | 100 |
| Sa-10 | S. aureus A20239 | 50 | 100 |
| Ec-1 | E. coli NIHJ | 25 | 100 |
| Ec-2 | E. coli P01495 | 25 | >100 |
| Ec-5 | E. coli ML1630 | 25 | 50 |
| Ec-9 | E. coli NR79/W677 | 12.5 | 25 |
| Ec-10 | E. coli JR35/C600 | 6.3 | 6.3 |
| Ec-49 | E. coli A20107 | 25 | 50 |
| Ec-53 | E. coli JR66/W677 | 25 | 25 |
| Ec-55 | E. coli R5 | 6.3 | 25 |
| Ec-62 | E. coli A20895 | 25 | 50 |
| Ec-72 | E. coli A20732 | 12.5 | 25 |
| El-2 | Ent. cloacae A20364 | 25 | 100 |
| El-12 | Ent. cloacae A21006 | 25 | 100 |
| Pv-1 | Pr. vulgaris A9436 | 25 | 100 |
| Pg-2 | Pr. morganii A20031 | 25 | 50 |
| Pm-1 | Pr. mirabilis A9554 | 25 | 50 |
| Ps-2 | Prov. stuartii A20894 | >100 | >100 |
| Kp-1 | K. pneumoniae D11 | 6.3 | 12.5 |
| Kp-8 | K. pneumoniae Type 22–3028 | 25 | 100 |
| Sm-1 | Ser. marcescens A20019 | >100 | >100 |
| Sm-16 | Ser. marcescens A21247 | >100 | >100 |
| Pa-3 | Ps. aeruginosa A9930 | 12.5 | 50 |
| Pa-12 | Ps. aeruginosa A20653 | 50 | >100 |
| Pa-16 | Ps. aeruginosa # 130 | 25 | 100 |
| Pa-21 | Ps. aeruginosa A20601 | 50 | >100 |
| Pa-24 | Ps. aeruginosa A20896 | 50 | >100 |
| Pa-27 | Ps. aeruginosa GN315 | 25 | 100 |
| Px-10 | Pseudomonas sp. A20621 | >100 | >100 |

Table 8
Effect Of Media pH On MIC Of Bu-2183 A

| Code No. | Strain | pH 6 | pH 7 | pH 8 | pH 9 |
|---|---|---|---|---|---|
| Ec-1 | E. coli NIHJ | >50 | 50 | 25 | 12.5 |
| Kp-1 | K. pneumoniae D 11 | 12.5 | 12.5 | 12.5 | 3.1 |
| Pa-1 | Ps. aeruginosa D 15 | >50 | 50 | 25 | 12.5 |
| Sa-10 | S. aureus Smith | >50 | 50 | 50 | 50 |
| Bs-1 | B. subtilis PCI 219 | 50 | 6.3 | 6.3 | 6.3 |

Table 9
Effect Of Media On Activity Of Bu-2183 A And B

| Code No. | Strain | Bu-2183 A NA* | HIA | MHA | Bu-2183 B NA | HIA | MHA |
|---|---|---|---|---|---|---|---|
| Ec-1 | E. coli NIHJ | 12.5 | 50 | 100 | 50 | >100 | >100 |
| Kp-1 | K. pneumoniae D11 | 3.1 | 12.5 | 25 | 12.5 | 50 | 50 |
| El-2 | Ent. cloacae A20364 | 25 | 50 | 100 | 50 | >100 | >100 |
| Pv-1 | Ps. vulgaris A9436 | 12.5 | 50 | 100 | 50 | >100 | >100 |
| Pm-1 | Ps. mirabilis A9554 | 12.5 | 50 | 50 | >100 | >100 | 100 |
| Pa-3 | Ps. aeruginosa A9930 | 12.5 | 25 | 50 | 25 | 100 | >100 |
| Sa-2 | S. aureus Smith | 12.5 | 50 | 50 | 50 | 100 | >100 |
| Sa-10 | S. aureus A20239 | 25 | 100 | >100 | 100 | >100 | >100 |

*NA : Nutrient agar
HIA : Heart infusion agar
MHA : Mueller-Hinton agar

Table 10
In Vivo Activity Of Bu-2183 A And B

| | PD$_{50}$ In Mg./Kg. (single dose) | |
|---|---|---|
| Infective Organism | Bu-2183 A | Bu-2183 B |
| S. aureus Smith | 42 | 100 |
| E. coli NIHJ | 92 | 135 |
| Ps. aeruginosa A9930 | 230 | 540 |

| | PD$_{50}$ In Mg/Kg. (double doses) |
|---|---|
| Infective Organism | Bu-2183 A |
| S. aureus Smith | 36 × 2 |
| E. coli NIHJ | 45 × 2 |
| Ps. aeruginosa A9930 | 80 × 2 |

The following examples are offered only for the purposes of illustrating the present invention and are not intended to limit same in any respect. Amberlite IRC-50 and CG-50 mentioned in the disclosure above and in the examples which follow are the trade names for weakly acidic cationic exchange resins of a carboxylic-polymethacrylic type.

EXAMPLE 1

(Fermentation In Tank)

Agar slant culture of Pseudomonas sp. strain D946-B83 was used to inoculate 100 ml. of seed medium No. 83B (3% glucose, 2% fish meal, 0.5% soybean meal, 0.2% peptone and 0.6% CaCO$_3$) in 500 ml. Erlenmeyer flasks. The flasks were incubated at 28° C. for 3 days on a rotary shaker (250 rpm) and 1 liter of the seed culture was used to inoculate 300 liters of fermentation medium No. 100F (2% glycerin, 1% Pharmamedia, 2% fish meal, 2% linseed meal, 0.3% (NH$_4$)$_2$SO$_4$, 0.6% CaCO$_3$). The tank was operated at 30° C. with stirring at 140 rpm and an aeration rate of 200 liters/minute. The broth potency was determined by the paper disc-agar plate method using B. subtilis PCI 219 as assay organism and Bu-2183 A as assay standard. The following results were obtained:

| Time (hrs.) | pH of Broth | Potency (mcg./ml.) |
|---|---|---|
| 0 | 6.7 | 0 |
| 20 | 7.5 | 200 |
| 30 | 7.8 | 400 |
| 40 | 7.9 | 1,600 |
| 50 | 7.9 | 1,650 |
| 60 | 8.1 | 1,700 |
| 64 | 8.1 | 1,800 |

EXAMPLE 2

(Extraction)

The harvested broth was filtered with filter aid at pH 2. The filtrate (19 liters) which contained about 30 grams potency of Bu-2183 A was adjusted to pH 7 and stirred with 3 liters of Amberlite IRC-50 (NH$_4$+ form). The resin was separated, washed with 10 liters of water and 5 liters of N/50 NH$_4$OH successively, and then stirred with two 4 liter-portions of N/2 NH$_4$OH to elute the bioactivity. The active eluates were combined, concentrated in vacuo and then lyophilized to afford 18.6 g. of white soli (about 700 mcg./mg.). This solid was dissolved in water and applied to a column of Amberlite CG-50 ($NH_4^+$ form, 400 ml.). The column was washed with 2.2 liters of water and 3 liters of N/40 $NH_4OH$ successively, and then developed with N/20 $NH_4OH$. The eluates were collected fractionally and examined by bioassay on *B. subtilis* plate and also by TLC (system S-117, ninhydrin). Appropriate fractions were combined, concentrated in vacuo and lyophilized to give the following solids.

| N/20 $NH_4OH$ | Solid Wt. | Bu-2183 Components (crude) |
|---|---|---|
| 0 – 1.3 liters | — | no activity |
| – 2.5 liters | 2.7 g. | A |
| – 4.4 liters | 7.8 g. | A + B (minor) |
| – 5.2 liters | 3.3 g. | B |

EXAMPLE 3

(Preparation of Bu-2183 A)

The crude sample of Bu-2183 A (2.7 g.) obtained in Example 2 was dissolved in water and applied to a column of Amberlite CG-50 ($NH_4^+$, 80 ml.). The column was eluted with N/20 $NH_4OH$ and each 15 ml. portion of the eluate was collected by a fraction collector. Fractions were examined by TLC-ninhydrin and also by bioassay, and appropriate fractions were combined, concentrated in vacuo and lyophilized to give the following solids.

| Fraction No. | Solid Wt. | TLC |
|---|---|---|
| 28 – 53 | 801 mg. | A + impurity |
| 54 – 72 | 1,597 mg. | A |
| 73 – 95 | 189 mg. | A + B (minor) |

The pure preparation of Bu-2183 A was analyzed for $C_{15}H_{31}N_3O_9 \cdot \frac{1}{2} H_2CO_3$:

Anal. Calc'd: C, 43.45; H, 7.53; N, 9.81. Found: C, 43.22; H, 7.52; N, 9.49.

Its IR and NMR spectra are shown in FIGS. 1 and 2, respectively. A summary of the NMR data is given below:

| Chemical Shift (δ, ppm) | Coupling Constant (J, Hz) | Relative Intensity |
|---|---|---|
| 1.12 t | 7.5 | 3H |
| 2.29 q | 7.5 | 2H |
| 3.1–3.35 m | | 2H |
| 3.5–4.3 m | | 12H |
| 5.17 d | 3.0 | 1H | s = singlet;
d = doublet;
t = triplet;
q = quartet;
m = multiplet

EXAMPLE 4

(Preparation Of Bu-2183 B)

The crude sample of Bu-2183 B (3.3 g.) obtained in Example 2 was dissolved in water and applied to a column of Amberlite CG-50 ($NH_4^+$, 130 ml.). The column was eluted with N/20 $NH_4OH$ and each 15 ml. portion of the eluate was collected by a fraction collector. Fractions were examined by TLC-ninhydrin and also by bioassay, and appropriate fractions were combined, concentrated in vacuo and lyophilized to give the following solids.

| Fraction No. | Solid Wt. | TLC |
|---|---|---|
| 1 – 59 | 86 mg. | B + impurity |
| 60 – 151 | 2,792 mg. | B |
| 152 – 160 | 356 mg. | B + impurity (minor) |

The pure preparation of Bu-2183 B was analyzed for $C_{14}H_{29}N_3O_9 \cdot \frac{1}{2} H_2CO_3$:

Anal. Calc'd.: C, 42.02; H, 7.30; N, 10.14. Found: C, 41.92; H, 7.43; N, 9.93.

Its IR and NMR spectra are shown in FIGS. 5 and 6, respectively. A summary of the NMR data is given below:

| Chemical Shift (σ, ppm) | Coupling Constant (J, Hz) | Relative Intensity |
|---|---|---|
| 2.02 s | | 3H |
| 3.1–3.2 m | | 2H |
| 3.6–4.3 m | | 12H |
| 5.17 d | 3.0 | 1H | s = singlet;
d = doublet;
m = multiplet

EXAMPLE 5

(Preparation of Bu-2183 C and Bu-2183 D)

The column used in Example 2 was further developed with 1.4 liters of N/20 $NH_4OH$, with which no more bioactive material was eluted. The column was then developed with N/10 $NH_4OH$ and the eluates were examined by TLC sprayed with ninhydrin reagent. Appropriate fractions were combined, concentrated in vacuo and lyophilized to give the following solids.

| N/10 $NH_4OH$ | Solid Wt. | Indentification |
|---|---|---|
| 0 – 300 ml. | — | |
| 301 – 1,200 ml. | 1,638 mg. | Bu-2183 C |
| 1,201 – 1,900 ml. | — | |
| 1,901 – 2,400 ml. | 526 mg. | Bu-2183 D |

EXAMPLE 6

(Preparation of Bu-2183 $A_2$)

During the purification process of component A described in Example 3, a new active component was isolated from forerun fractions and designated as component Bu-2183 $A_2$. It was differentiated from component A by the TLC systems S-117 and S-122 as shown below:

| | Bu-2183 A | Bu-2183 $A_2$ |
|---|---|---|
| S-117 | Rf = 0.49 | Rf = 0.57 |
| S-122 | Rf = 0.39 | Rf = 0.48 |

The Ir and NMR spectra of component Bu-2183 $A_2$ are shown in FIGS. 3 and 4. A summary of the NMR data is given below:

| Chemical Shift (σ, ppm) | Coupling Constant (J, Hz) | Relative Intensity |
|---|---|---|
| 0.92 t | 7.5 | 3H |
| 1.63 sixtet | 7.5 | 2H |
| 2.30 t | 7.5 | 2H |
| 3.1–3.5 m | | 2H |
| 3.6–4.4 m | | 12H |

| Chemical Shift (σ, ppm) | Coupling Constant (J, Hz) | Relative Intensity |
|---|---|---|
| 5.27 d | 3.0 | 1H | d = doublet;
t = triplet;
m = multiplet

We claim:

1. A process for producing the antibiotic complex Bu-2183 which comprises cultivating Pseudomonas sp. strain D946-B83, A.T.C.C. 31086, in an aqueous nutrient medium containing assimilable sources of nitrogen and carbon under submerged aerobic conditions until a substantial amount of Bu-2183 is produced by said organism in said culture medium.

2. The process of claim 1 which includes the further step of recovering the Bu-2183 complex from the culture medium.

3. The process of claim 1 which includes the separation of the Bu-2183 complex into the individual components Bu-2183A, Bu-2183B, Bu-2183A$_2$ and Bu-2183D by the steps of
    (a) separating the Bu-2183 complex from the mycelium;
    (b) adsorbing the complex on a cationic ion-exchange resin;
    (c) fractionally eluting the Bu-2183 components from the adsorbent; and
    (d) recovering the fractions of the desired components Bu-2183A, B, A$_2$ and D.